(12) United States Patent
Kehr et al.

(10) Patent No.: US 7,087,067 B2
(45) Date of Patent: Aug. 8, 2006

(54) SURGICAL SCALPEL WITH PROTECTIVE SHEATH

(75) Inventors: Rajiv Kehr, Kanpur (IN); Scott Larsen, Newton, CT (US)

(73) Assignee: Kehr Surgical Private Ltd., Kanpur, IN (US)

( * ) Notice: Subject to any disclaimer, the term of this patent is extended or adjusted under 35 U.S.C. 154(b) by 247 days.

(21) Appl. No.: 10/684,068

(22) Filed: Oct. 9, 2003

(65) Prior Publication Data

US 2004/0181247 A1 Sep. 16, 2004

Related U.S. Application Data

(60) Provisional application No. 60/417,463, filed on Oct. 9, 2002.

(51) Int. Cl.
*A61B 17/32* (2006.01)

(52) U.S. Cl. .................. 606/167; 30/143; 30/136.5

(58) Field of Classification Search ............... None
See application file for complete search history.

(56) References Cited

U.S. PATENT DOCUMENTS

| | | | |
|---|---|---|---|
| 2,215,125 A | 9/1940 | Maltz | |
| D165,338 S | 12/1951 | McNutt | |
| D223,795 S | 6/1972 | Covey | |
| 3,906,626 A * | 9/1975 | Riuli ..................... | 30/162 |
| D270,372 S | 8/1983 | Russo et al. | |
| 4,719,915 A | 1/1988 | Porat et al. | |
| 4,823,457 A | 4/1989 | Prochaska | |
| D305,096 S | 12/1989 | Tench et al. | |
| D327,125 S | 6/1992 | Iten | |
| 5,207,696 A | 5/1993 | Matwijow | |
| D336,029 S | 6/1993 | Ragland et al. | |
| 5,254,128 A | 10/1993 | Mesa | |
| 5,299,357 A | 4/1994 | Wonderley et al. | |
| 5,309,641 A * | 5/1994 | Wonderley et al. ........... | 30/339 |
| 5,330,493 A | 7/1994 | Haining | |
| D352,882 S | 11/1994 | Schmidt | |
| 5,417,704 A | 5/1995 | Wonderley | |
| D360,817 S | 8/1995 | Moyer, Jr. et al. | |
| 5,475,925 A | 12/1995 | Newman et al. | |
| 5,478,346 A | 12/1995 | Capewell | |
| 5,481,804 A | 1/1996 | Platts | |
| 5,527,329 A | 6/1996 | Gharibian | |
| 5,531,754 A | 7/1996 | Shackelford, Sr. et al. | |
| 5,571,127 A | 11/1996 | DeCampli | |
| 5,571,128 A | 11/1996 | Shapiro | |
| 5,599,351 A | 2/1997 | Haber et al. | |
| 5,662,669 A | 9/1997 | Abidin et al. | |
| 5,665,099 A | 9/1997 | Pilo et al. | |
| 5,676,677 A | 10/1997 | Landis et al. | |
| 5,730,751 A * | 3/1998 | Dillon et al. ................ | 606/167 |

(Continued)

*Primary Examiner*—Glenn K. Dawson
(74) *Attorney, Agent, or Firm*—Greenberg Traurig LLP

(57) ABSTRACT

A protective sheath for a disposable surgical scalpel includes at least three modes of operation, (i) a protective mode, (ii) an open mode, and (iii) a permanently locked mode. In the open mode, a locking strip of the scalpel handle resides in one opening of the sheath to keep the sheath substantially immobile during use of the scalpel blade. In the protective mode, the locking strip resides in a second opening of the sheath to keep the sheath substantially immobile when the scalpel blade is not in use. In the permanently locked mode, a button connected to the sheath is depressed into the second opening and engages the locking strip, thereby preventing the blade from being used and allowing the scalpel to be safely disposed.

20 Claims, 14 Drawing Sheets

U.S. PATENT DOCUMENTS

| | | |
|---|---|---|
| 5,749,886 A | 5/1998 | Abidin et al. |
| 5,779,724 A | 7/1998 | Werner |
| 5,797,940 A | 8/1998 | Mawhirt et al. |
| D399,720 S | 10/1998 | Owens et al. |
| 5,827,309 A | 10/1998 | Jolly et al. |
| 5,843,107 A | 12/1998 | Landis et al. |
| 5,868,771 A | 2/1999 | Herbert et al. |
| 5,908,432 A | 6/1999 | Pan |
| 5,919,201 A | 7/1999 | Carter et al. |
| 5,938,675 A | 8/1999 | Gharibian |
| 5,941,892 A | 8/1999 | Cohn et al. |
| 6,015,419 A | 1/2000 | Strome et al. |
| 6,022,364 A | 2/2000 | Flumene et al. |
| 6,053,929 A | 4/2000 | Cohn et al. |
| 6,254,621 B1 | 7/2001 | Shackelford et al. |
| 6,263,577 B1 | 7/2001 | Wonderley |
| D455,061 S | 4/2002 | Huang |
| 2002/0056198 A1 | 5/2002 | Ping |

* cited by examiner

SURGICAL SCALPEL WITH PROTECTIVE SHEATH

RELATED APPLICATIONS

This application is related to U.S. Provisional Application Ser. No. 60/417,463 entitled "Surgical Scalpel with Protective Sheath" which was filed on Oct. 9, 2002, and is incorporated by reference herein in its entirety.

BACKGROUND OF THE INVENTION

1. Field of the Invention

The present invention relates to a surgical scalpel and particularly relates to a scalpel having a handle, a blade, and a sheath movable along the scalpel handle between a protective position overlying and covering the blade and a retracted position exposing the blade for use.

2. General Background and State of the Art

Disposable scalpels are well known in the art and often comprise a handle, typically formed of a plastic material, to which is attached either permanently or detachably, a scalpel blade. Such disposable scalpels are conventionally packaged in sterile containers, e.g., flexible plastic packages or pouches. Once removed from the container, the blade is typically exposed for use. This, of course, also exposes the blade to all individuals, doctors, nurses, medical technicians, etc., associated with a surgical procedure, as well as those individuals charged with the disposal of the used scalpel. Thus, even with the exercise of great care, individuals are frequently inadvertently cut by the exposed blade. The dangers of being cut and transmission of infectious diseases when cut by a used blade are thus ever-present. Even when using scalpels having blades which are detached after use and disposed in a sharps container, those individuals handling the scalpels, blades or sharps containers remain at risk.

Disposable safety scalpels have been developed with these problems in mind. The results generally fall into two categories: retractable blade scalpels, which provide for a blade that fully retracts into the handle, and sliding sheath scalpels, which provide for a cover which slides over the blade.

SUMMARY OF THE INVENTION

It is an object of the present invention to provide a scalpel having a protective sheath that will cover the blade reliably when the scalpel is not in use (i.e., an extended protective mode for the cover/sheath), uncover the blade when the scalpel is in use (i.e., an open retracted mode for the cover/sheath), and permanently lock the scalpel when it is ready for disposing (a permanently locked mode). Furthermore, the sheath should be firmly held against the handle so that it cannot automatically move between different operating modes of the scalpel. This feature is desirous in various environments (e.g., in an operating room during a surgical procedure). Furthermore, the scalpel should be designed to be sturdy and reliable, and manufactured using high quality materials.

The disposable scalpel of the present invention allows for three modes of operation: an open position, a closed position, and a permanently closed and locked position. The open position exposes the blade for use and holds the sheath in a retracted position. The closed position protects and covers the blade, yet still allows for movement into the open position when necessary. The permanently closed and locked position prevents the sheath from moving again, and allows for safe and proper disposal of the scalpel.

The handle has a flexible locking strip which engages the sheath, in two openings, in an opened and closed position. The first opening lies below the release button and is used for receiving a locking strip when the sheath is retracted (i.e., open position). This feature prevents the sheath from moving when the sheath is retracted, thereby allowing a user to operate the blade comfortably. The second opening in the sheath also receives the flexible locking strip and prevents the sheath from sliding back when the scalpel blade is not in Use. The second opening also allows the scalpel to be locked out by means of a lockout button when the sheath is in the extended/closed position (i.e., scalpel blade is covered). The sheath also has a first button for releasing the flexible locking strip from the first opening and allowing the sheath to move from the open position to the closed position.

In order to retract the sheath for operation, the user must apply sufficient force on the sheath to overcome the flexible locking strip, which is shaped in a way to be deflected when sufficient force is applied. The sheath is held in the open position when the flexible locking strip advances past the solid portion of the sheath to the button located on the top portion of the sheath. The flexible locking strip again engages the sheath through an open portion, resting just under the button on the top portion of the sheath.

To cover the blade, one must apply pressure to the button on the top portion of the sheath to displace the flexible locking strip and move the sheath forward. The scalpel may be re-opened and closed again thereby allowing multiple use.

To permanently close and lock the sheath, in order to properly dispose of the scalpel, one depresses the button on the side of the sheath into an opening which has the flexible locking strip. One side of the button on the sheath engages with one side of the flexible locking strip of the handle to lockout the scalpel, thereby preventing any further use of said scalpel. In one aspect, the button may have a lockout feature. Thus, upon depressing the button on the sheath, this lockout feature on the button fits into an opening and engages one side of the flexible strip This then prevents the lock out button on the sheath from springing back out once engaged with the flexible locking strip. Furthermore, this then prevents the flexible locking strip from flexing downwards and permitting the sheath from moving in any direction.

In summary, this lockout mechanism prevents the sheath from moving in any direction thereby effectively locking the scalpel. The blade is now safely covered and permanently locked for disposal.

Accordingly, in one embodiment of the present invention, the disposable scalpel comprises: (i) a handle; (ii) a surgical blade attached to one end of the handle; (iii) a sheath covering at least a portion of the handle, movable between two positions: an open position wherein the blade is at least partly uncovered and available for use; and a closed position wherein the blade is substantially covered and not available for use; (iv) a flexible locking strip attached to the handle for engaging the sheath in the open and closed positions; (v) a first button attached to the sheath for releasing the flexible locking strip and allowing the sheath to be moved between the open and the closed position; and (vi) a second button attached to the sheath for permanently locking the sheath in the closed position. Alternatively, the flexible locking strip may be part of the sheath and may be used for engaging the sheath in an open and closed positions.

In another embodiment of the present invention the locking mechanism, for the permanently closed and locked position, allows a spring-operated button associated with the handle to engage an opening associated with the sheath. For example, as soon as the sheath passes a predetermined position, to cover the blade, the spring activates the button to automatically engage the opening in the sheath thereby locking the sheath. Moreover, a notch or the like, either on the handle or the sheath, may engage the button at this point to prevent the button from being depressed, thus preventing the scalpel from being used again.

DESCRIPTION OF THE PREFERRED EMBODIMENTS

Figure 1A:
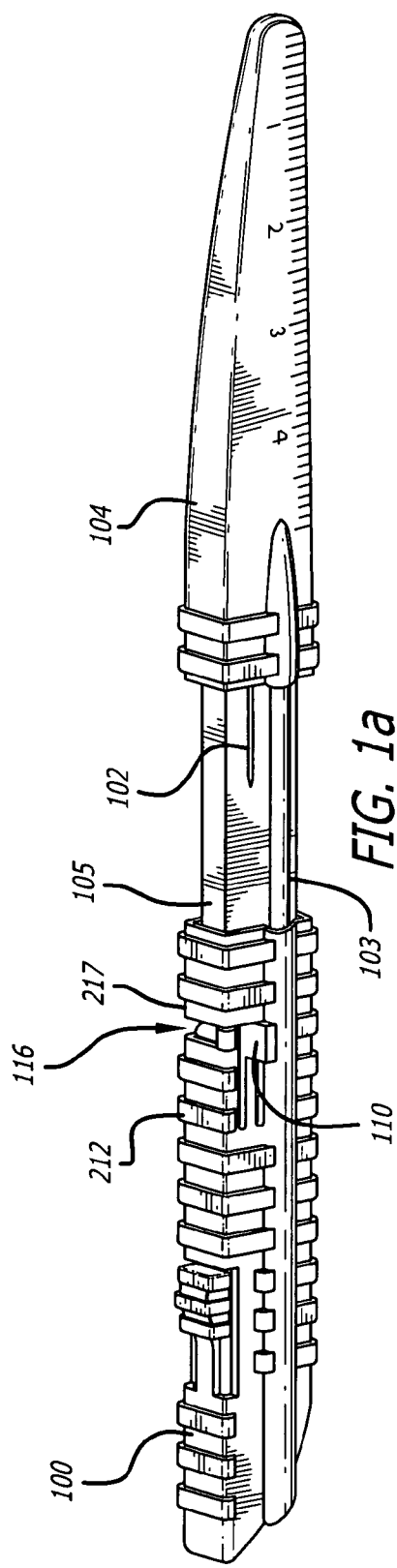
FIG. 1a is a perspective view of the scalpel of the present invention in an extended protective mode (i.e., closed position) where the sheath covers the blade.
Figure 1B:
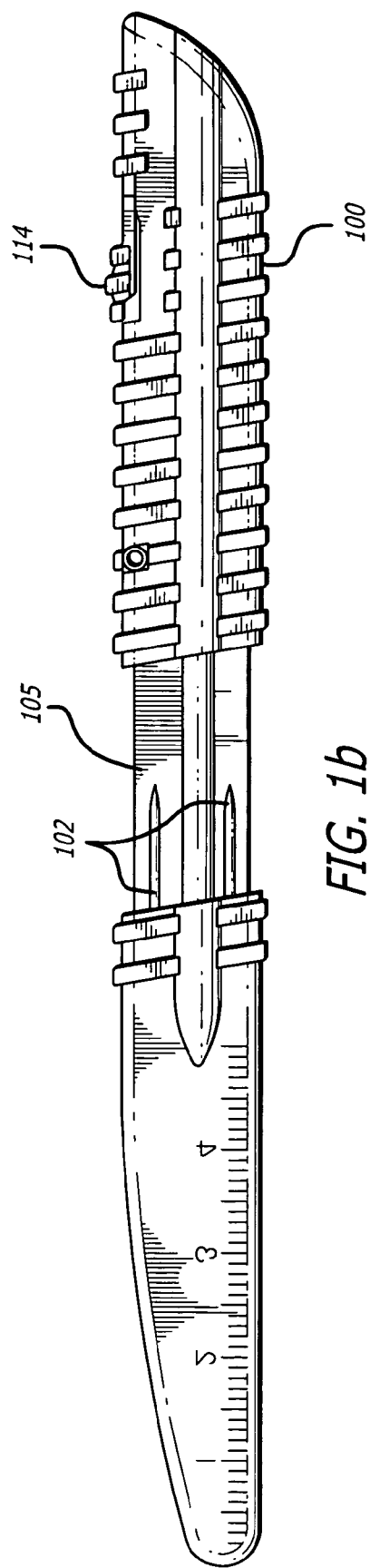
FIG. 1b is another view of the scalpel of the present invention in the closed position.

Reference will now be made in detail to an exemplary embodiment of the present invention, an example which is illustrated in the accompanying drawings FIGS. 1–17. It is to be understood that other embodiments may be utilized and structural and functional changes may be made without departing from the respective scope of the present invention.

Referring now to FIGS. 1, 4, 5, 6 a scalpel having a first and a second handle portion 104 and 105 respectively, a sheath portion 100, and a blade portion 101 in accordance with one aspect of the present invention is shown. FIGS. 1a, 1b, 1c, and 4 show the scalpel with the sheath portion 100 in an extended or protective mode (i.e., closed position), covering the blade 101. FIGS. 1d, 1e, 1f, 1g, 5, 6 show the scalpel with the sheath 100 in a retracted or uncovered mode (i.e., in an open position) where the blade 101 exposed. Rails 103 on each side of the handle portion 105 provide guidance for the sheath 100 to move along the handle portion 105. The handle portion 105 also has mini-rails 102, on each side, for providing a snug fit of the sheath 100 with the handle portion 105.

The handle portion 105 has a flexible locking strip 112 which engages the sheath 100 in the opened and closed positions. This feature of the locking strip 112 prevents the sheath from moving when the sheath is in the extended/protective mode (i.e., in the closed position) or in the retracted mode.

Figure 1C:
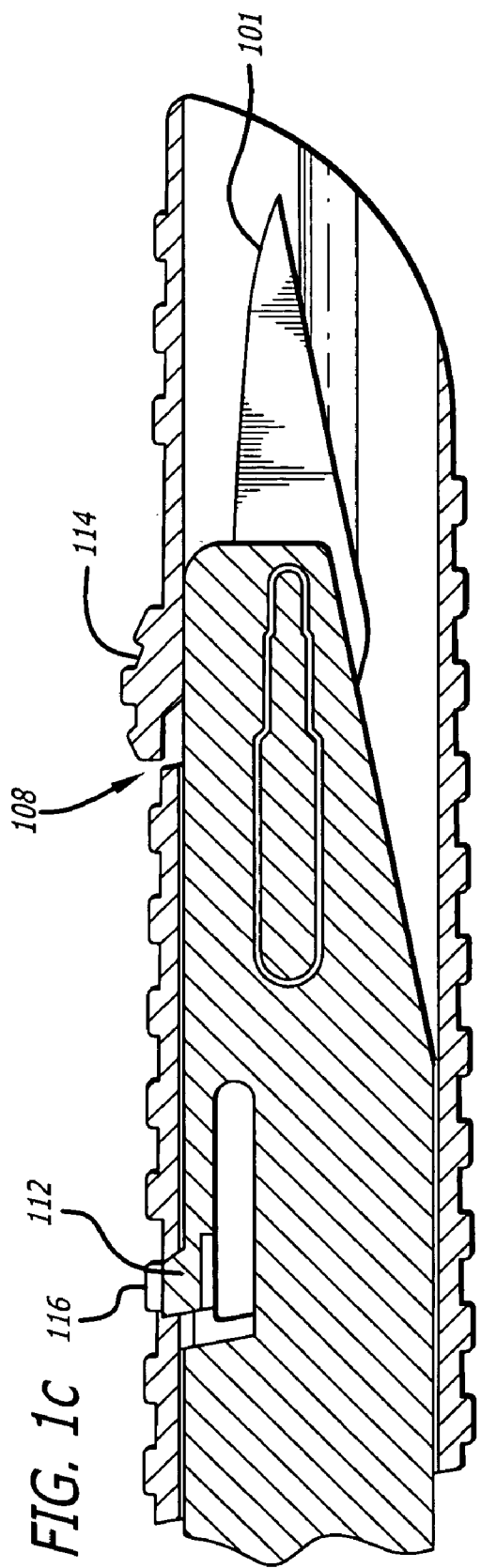
FIG. 1c is a side view of the scalpel of the present invention, in a closed position, depicting the flexible locking strip.
Figure 1D:
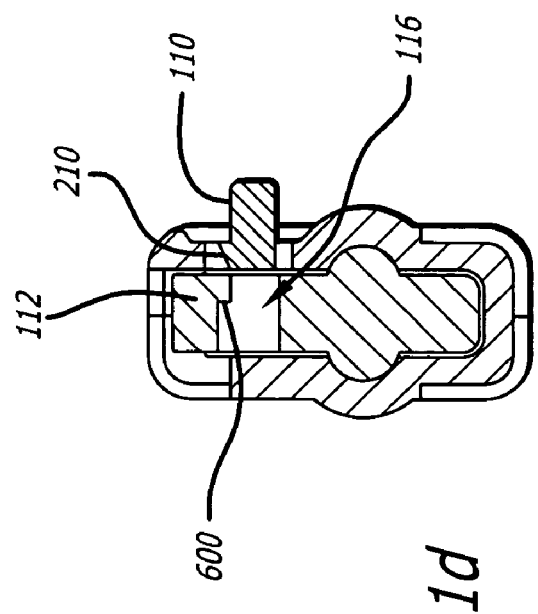
FIG. 1d is a cross sectional front view of the scalpel depicting the button used for permanently locking the sheath to the handle.
Figure 1E:
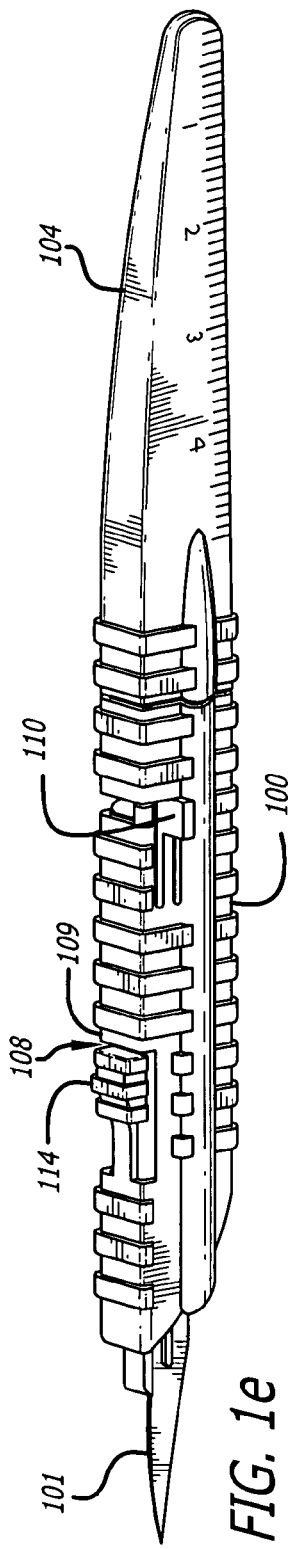
FIG. 1e is a perspective view of the scalpel of the present invention in a retracted mode (i.e., an open position) where the sheath uncovers the blade.
Figure 1F:
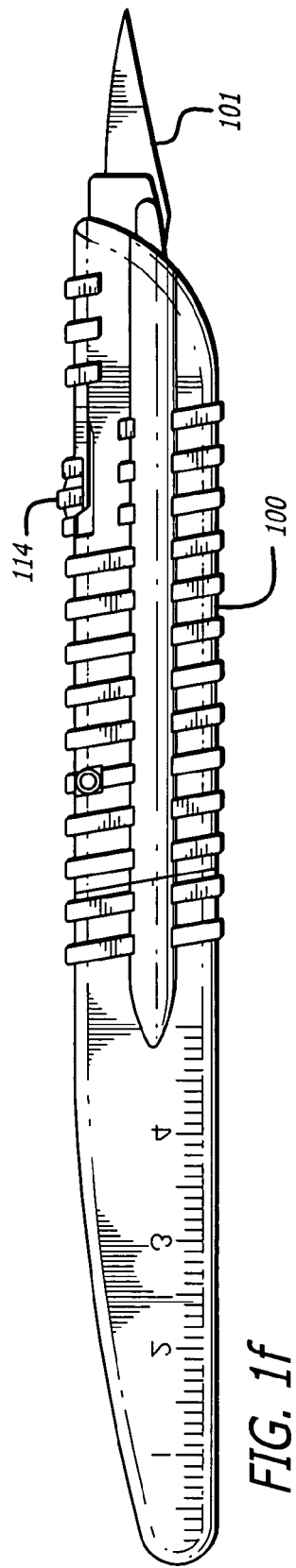
FIG. 1f is another view of the scalpel of the present invention in an open position where the sheath uncovers the blade.
Figure 1G:
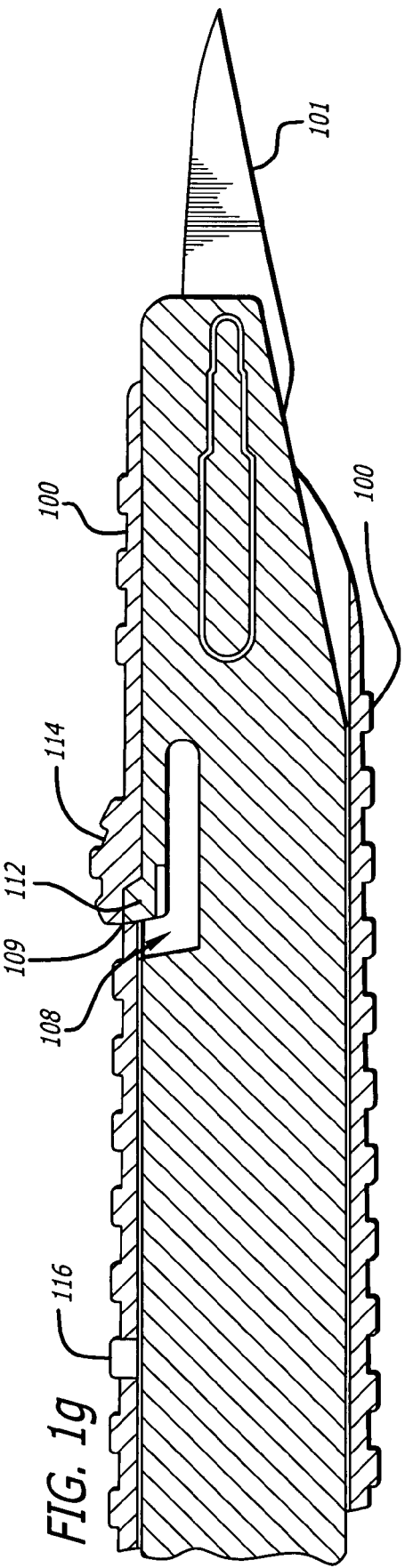
FIG. 1g is a side view of the scalpel of the present invention, in an open position, depicting the flexible locking strip.
Figure 2:
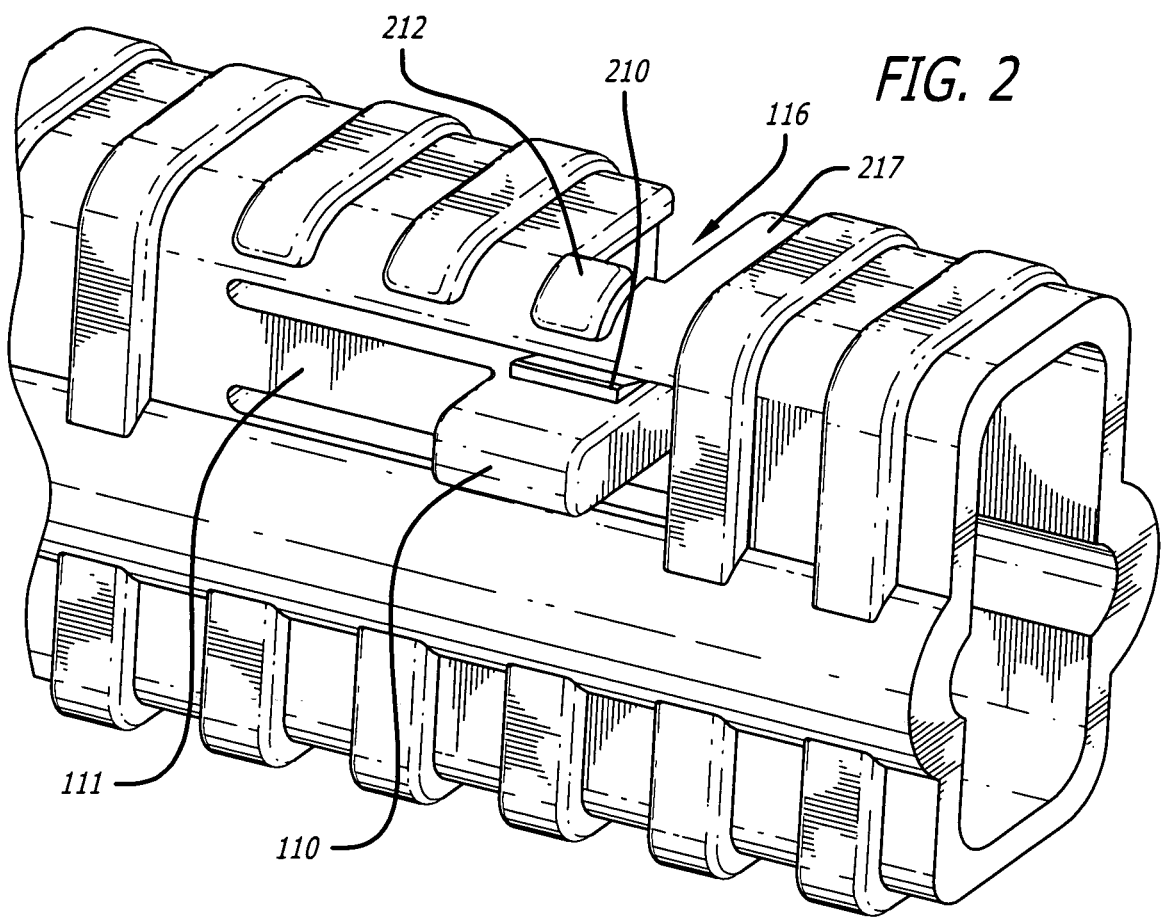
FIG. 2 is a close-up view of the button for permanently locking the sheath in the closed position.
Figure 3:
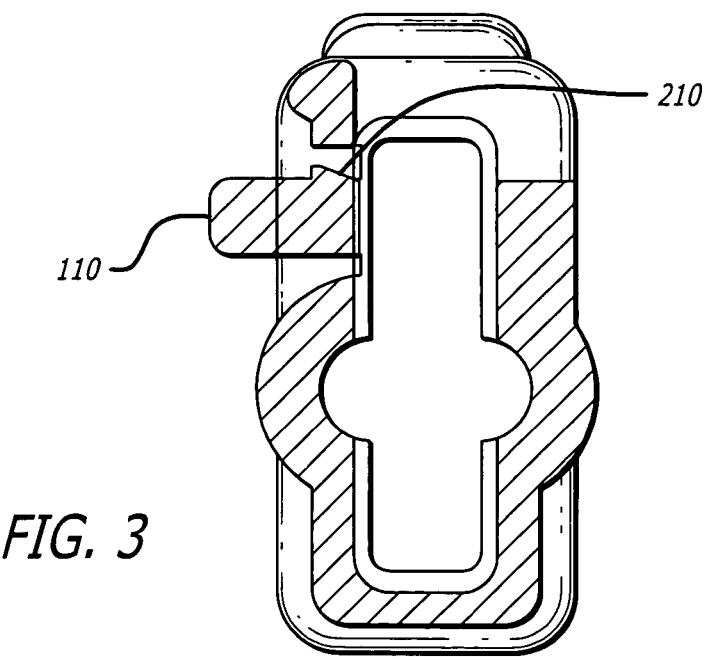
FIG. 3 is a cross-sectional view of the sheath having the button for permanently locking the sheath to the handle to prevent further use of the scalpel.
Figure 4:
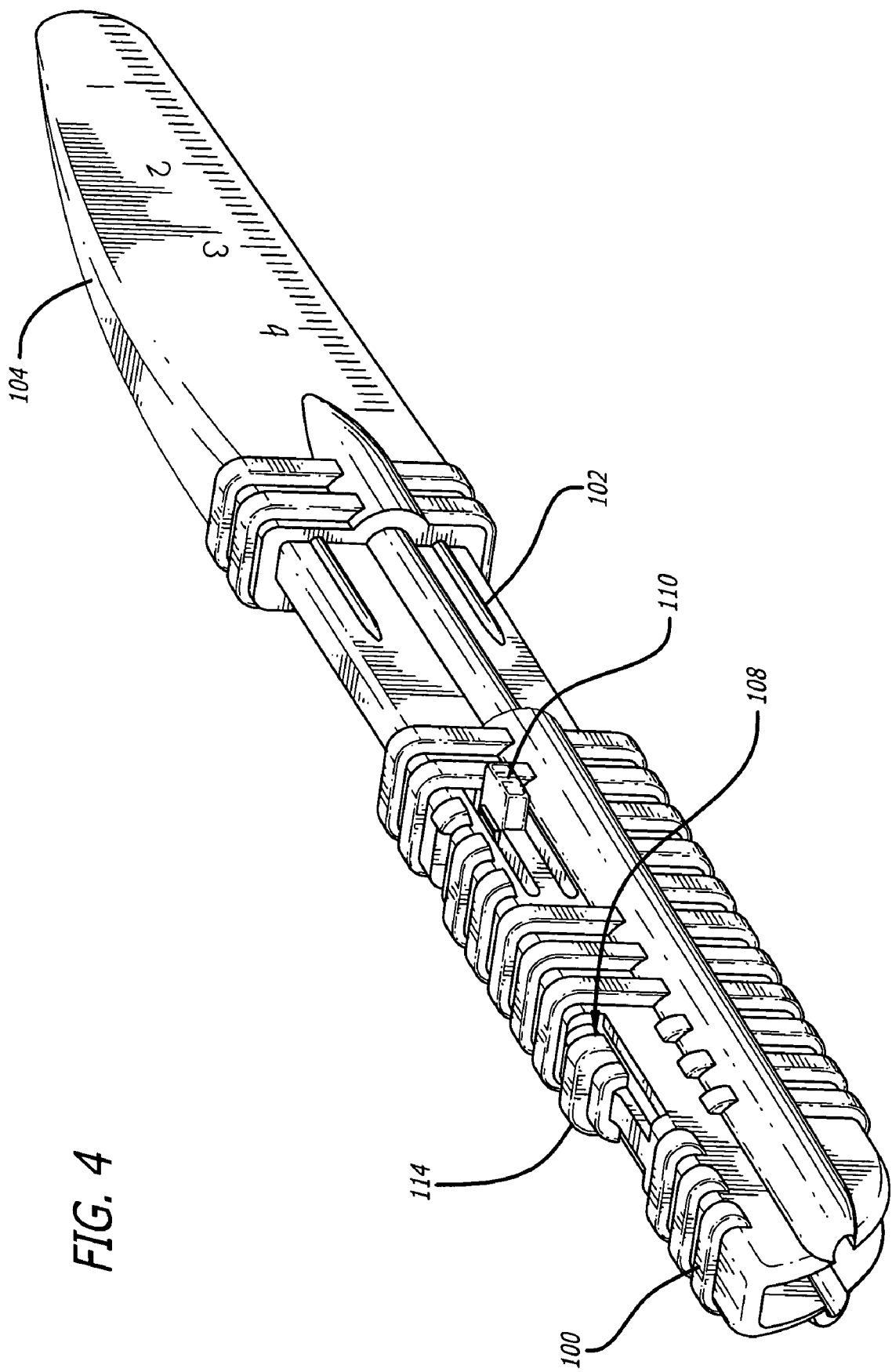
FIG. 4 is a view showing the snug fit of sheath over the handle.
Figure 5:
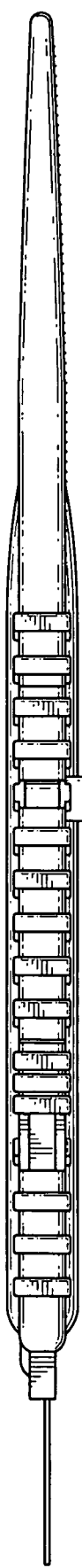
FIG. 5 is an elevation view of the scalpel, in the open position, of the present invention.
Figure 6:
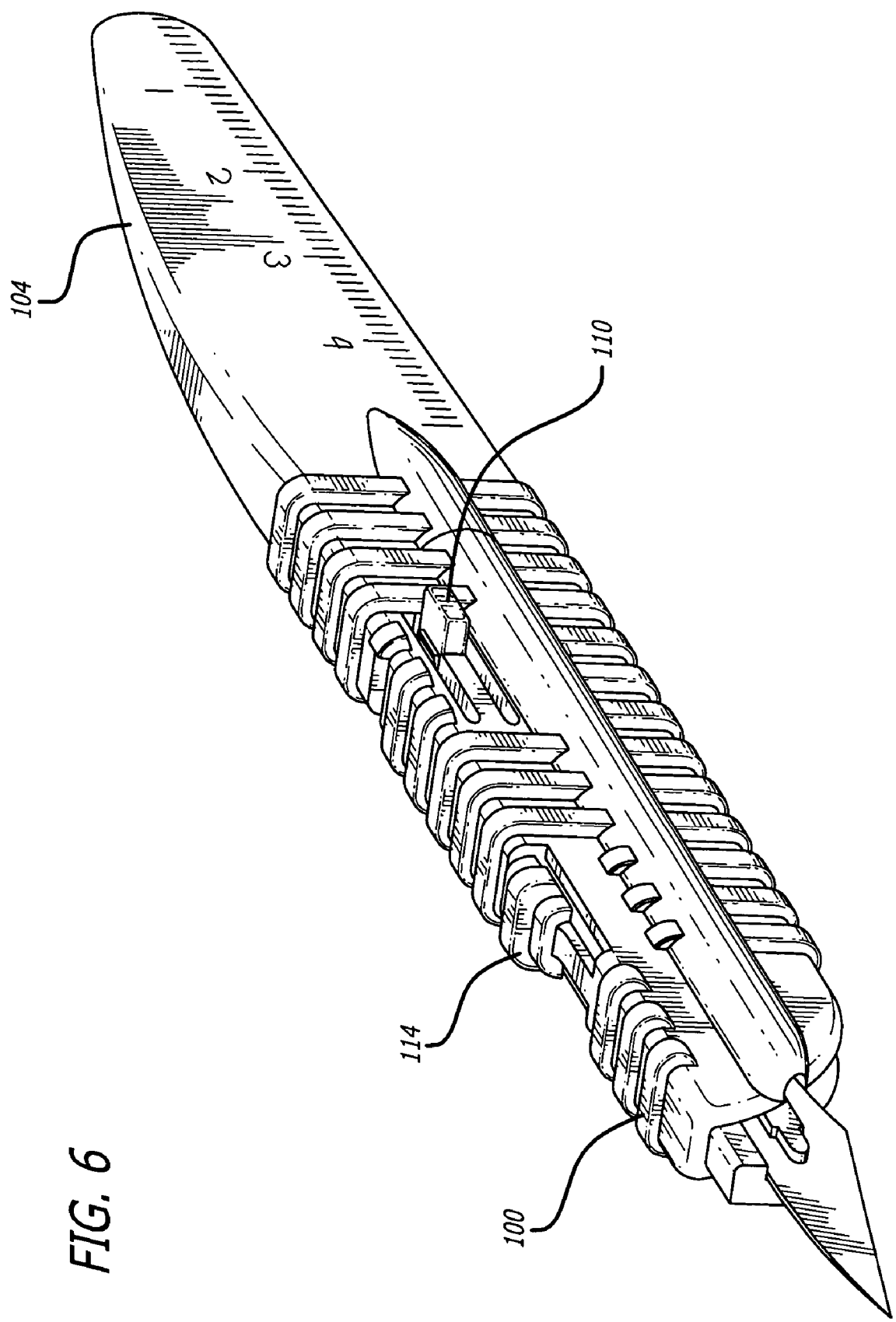
FIG. 6 is a view of scalpel of the present invention with the sheath retracted.
Figure 7:
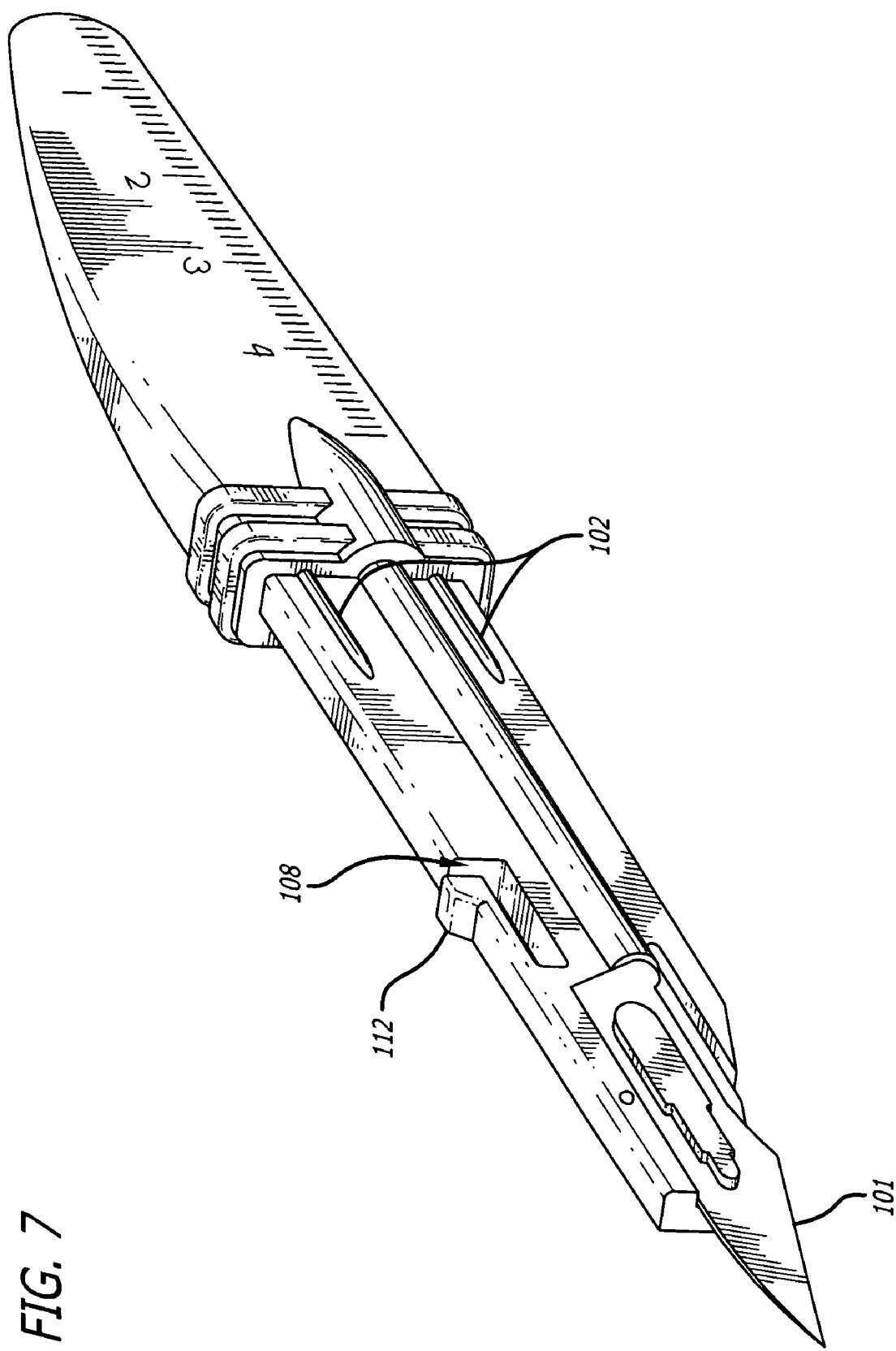
FIG. 7 is a view of the handle and blade arrangement without the protective sheath.

With reference to FIGS. 1e and 1g, when the sheath 100 is in a retracted mode or open position, the flexible locking strip 112, of the handle portion 105, sits in the opening 108 engaged on one side with the release button 114 and on another side with a wall 109 of the sheath 100. This intermediate locking arrangement of the sheath 100 to the handle portion 105 prevents the sheath 100 from moving when the blade 101 is being used. In order to move the sheath, from this intermediate lock position, a downward force is required to push the release button 114 so as to release the sheath 100 from its engaged position in the opening 108. Once this is done, a subsequent forward force, applied to the release button 114, will move the sheath 100 to a closed position (where the sheath 100 covers the blade 101).

With reference to FIGS. 1a and 1c, when the sheath 100 is in an extended, mode or closed position, the flexible locking strip 112, of the handle portion 105, sits in the opening 116 engaged with at least one wall of the sheath opening 116. This locking arrangement, of the sheath 100 to the handle portion 105, prevents the sheath 100 from moving when the blade 101 is covered, and also prevents the sheath 100 from falling off. By gripping the sheath with the thumb and placing the forefinger behind the release button 114, the sheath may again be moved to a retracted position, where the flexible locking strip is received in opening 108, thereby allowing the use of blade 101.

Thus, the scalpel may be used safely, a number of times during surgery, by moving the sheath to the intermediate positions using the flexible locking strip 112 and the sheath openings 108 and 116.

The sheath 100 is also designed with raised textured bumps or ribs 212 for better gripping with the hand. This is especially important when one considers that doctors and surgeons wear latex gloves which reduces sensation, and often are exposed to blood and fluids that may create a slippery surface.

With reference to FIGS. 1a, 1d, 2, and 3, shown therein is a permanent locking arrangement that prevents the blade 101 from being exposed again, thereby allowing safe disposal of the scalpel in an appropriate container (not shown). Specifically, when the sheath 100 is in the extended position (i.e., covering the blade), one depresses the permanent locking button 110 on the sheath 100 into the opening 116. With this, the wedge portion 210, of the button 110, slides into the opening 116 and engages a side wall 600 of the flexible locking strip 112. This prevents this lock out button 110 on the sheath from springing back out once engaged with the flexible locking strip 112. thus, this mechanism prevents: (i) the flexible locking strip from flexing downwards and (ii) the sheath from moving in any direction. The blade 101 is now safely covered and permanently locked allowing for the disposal of the scalpel.

In summary, the disposable scalpel of the present invention allows for three modes of operation: an open position, an intermediate closed position, and a permanently closed and locked position. The open position exposes the blade for use and holds the sheath in a retracted position. The intermediate closed position protects and covers the blade, yet still allows for movement into the open position when necessary. The permanently closed and locked position prevents the sheath from being opened again, and allows for safe and proper disposal of the scalpel.

The scalpel is preferably shipped in individually wrapped packages such sterilized plastic wrapping or pouch. When removed from packaging, the scalpel is in the closed position. The sheath is held in the closed position by the flexible locking strip engaging with an opening in the sheath.

In another embodiment of the present invention, the locking mechanism, for the permanently closed and locked position, allows a spring-operated button associated with the handle to engage an opening associated with the sheath. For example, as soon as the sheath passes a predetermined position, to cover the blade, the spring activates the button to automatically engage the opening in the sheath thereby locking the sheath. Moreover, a notch or the like, either on the handle or the sheath, may engage the button at this point to prevent the button from being depressed, thus preventing the scalpel from being used again.

The handle of the present invention is preferably made of cycoloy (PC/ABS) grade C 1200 HF. The sheath is preferably made of LEXAN (polycarbonate) grade HF 1130R/HF 1140R. These materials have been selected on the basis of suitability, however, other high end materials offering good strength, grip, and stiffness may be used as well.

Figure 8:
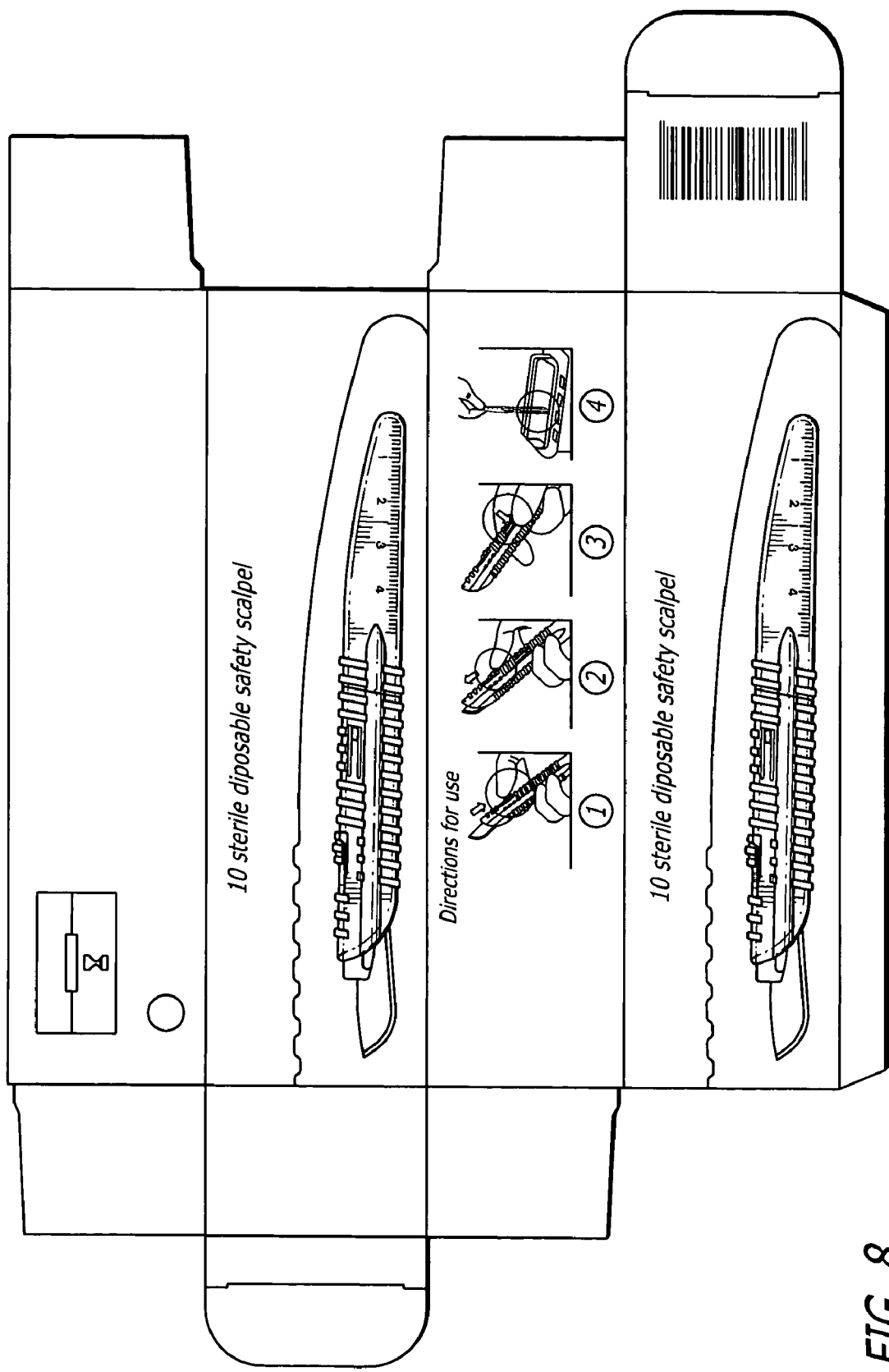
FIG. 8 is an exemplary embodiment of the packaging for the present invention showing directions for use.

FIG. 8 is an exemplary embodiment of the packaging for the present invention showing directions for use. Specifically, in step 1 the user is instructed to grip the sheath with the thumb and place the forefinger behind the release button 114 to retract the sheath 100 back so as to use the blade. The sheath is retracted until the flexible locking strip 112 sits in the opening 108 thereby temporary locking the sheath to the handle in an intermediate position (see FIG. 1g). In step 2, the user is instructed to extend the sheath, by pressing the release button 114, so as to cover the blade. In this case, the sheath is displaced until the flexible locking strip 112 is seated in the opening 116 (see FIG. 1a), thereby temporary locking the sheath to the handle in an intermediate position. If the user wishes to use the scalpel, he or she retracts the sheath as per step 1. In step 3, the user is instructed to lock the sheath to the handle by depressing the lock button 110 (see FIGS. 2, 3) thereby disabling the scalpel and preventing it from being used. In step 4, the user is instructed to dispose the disabled scalpel in an appropriate sharps container.

Figure 9A:
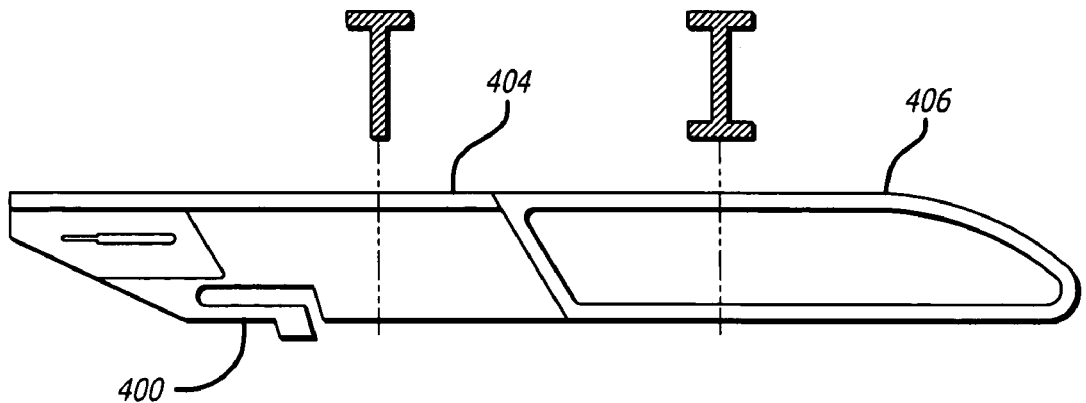
FIG. 9a is a side view of the scalpel handle according to another aspect of the present invention depicting the flexible locking or snap strip.
Figure 9B:
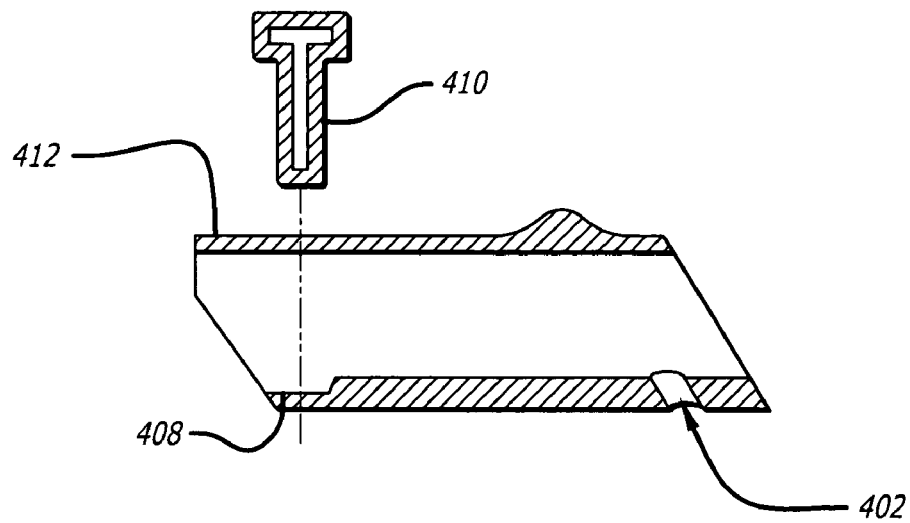
FIG. 9b is a side view of the scalpel sheath according to another aspect of the present invention depicting the sheath with a latch cutout for engaging the flexible locking strip of the handle.

FIGS. 9a and 9b show a side view of the scalpel handle 406 and the sheath 412, according to another aspect of the present invention, with a flexible locking or snap strip 400. The system for moving the sheath forward from the retracted (i.e., open) position to the extended (i.e., closed) position, in this embodiment, does not require the release button to be pressed to release the locking strip. The cross section profile of the handle and sheath is a "T" shape 410 which allows the stiffening and sheath support extend further along the handle without interfering with the cutting blade. The handle has a snap finger 400 similar to the locking strip but is placed on the bottom of the handle. The snap finger 400 provides two stop positions for the sheath. In this design the sheath be able to push over the snap finger to slide forward without having to release the snap finger. By adjusting the angle of the front ramp 408, on the sheath, it is possible to tune in a desired resistance for smooth sliding of the sheath along the handle. The back of the sheath 412 has a window feature 402 to prevent the sheath from falling off. Thus the sheath can be pushed forward, to cover the blade until the snap finger 400 rests in the latch cutout window 402.

Figure 10:
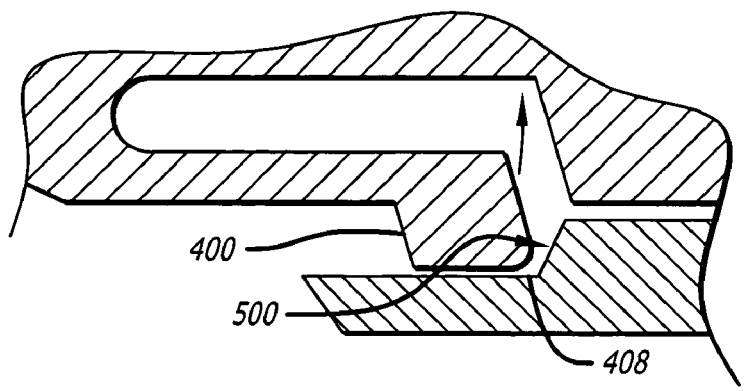
FIG. 10 is a side view showing the relationship of the flexible locking strip and the scalpel handle when the sheath is in a retracted position (i.e., open position)

FIG. 10 is a side view showing the relationship of the flexible locking strip and the scalpel handle when the sheath is in a retracted position (i.e., open position). The figure shows the flexible snap finger 400 sitting in a pocket 500 of the sheath when the sheath is retracted. The figure also shows the angled surface of the ramp 408, inside the sheath, that permits the flexible snap finger to slide and be depressed when the sheath is moved forward.

Figure 11:
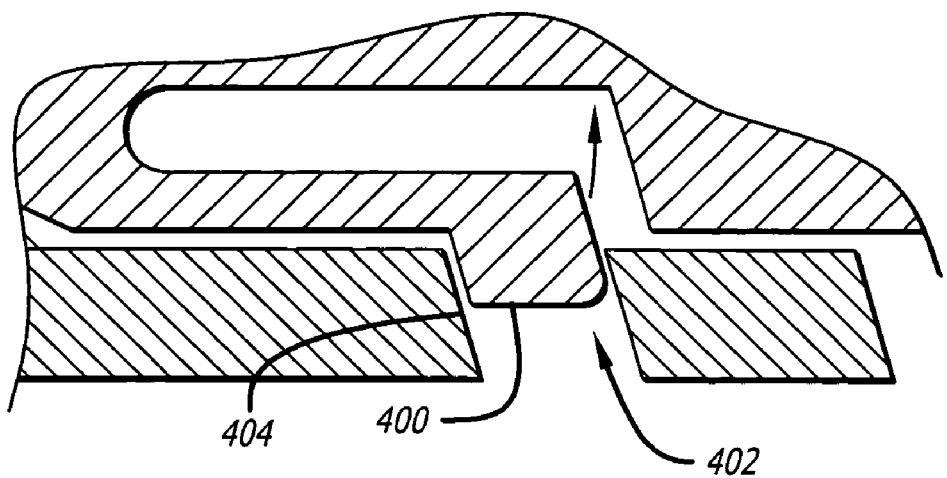
FIG. 11 is a side view showing the relationship of the flexible locking strip and the scalpel handle when the sheath is in an extended position (i.e., in a protective mode)

FIG. 11 is a side view showing the relationship of the flexible locking strip and the handle when the sheath is in an extended position (i.e., in a protective mode). Specifically, the figure shows a local detail of the sheath interface with the snap finger 400 when the sheath is in an extended position (i.e., the blade is covered). In this case, the flexible snap finger sits in the window 402 of the sheath. Furthermore, the ramped surface 404 inside the sheath is angled to push the flexible snap finger for allowing the sheath to slide back.

Figure 12:
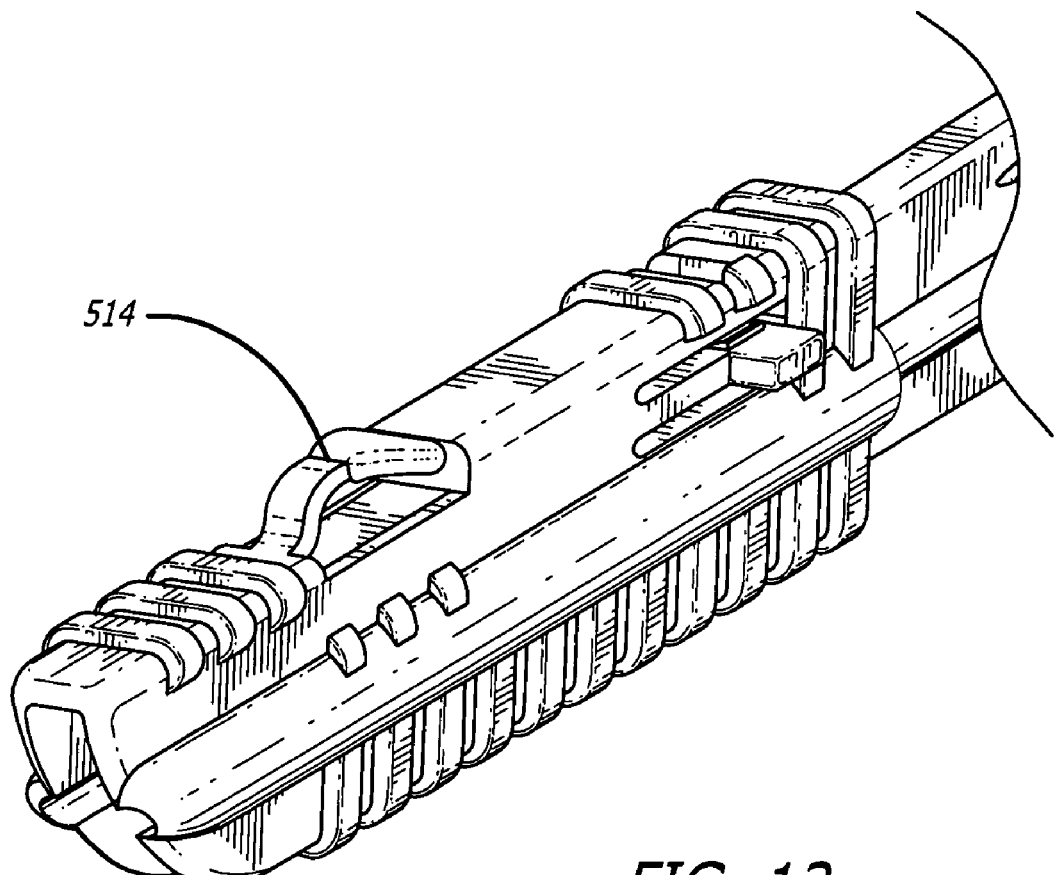
FIG. 12 is a view of a scalpel in another aspect of the present invention.
Figure 13:
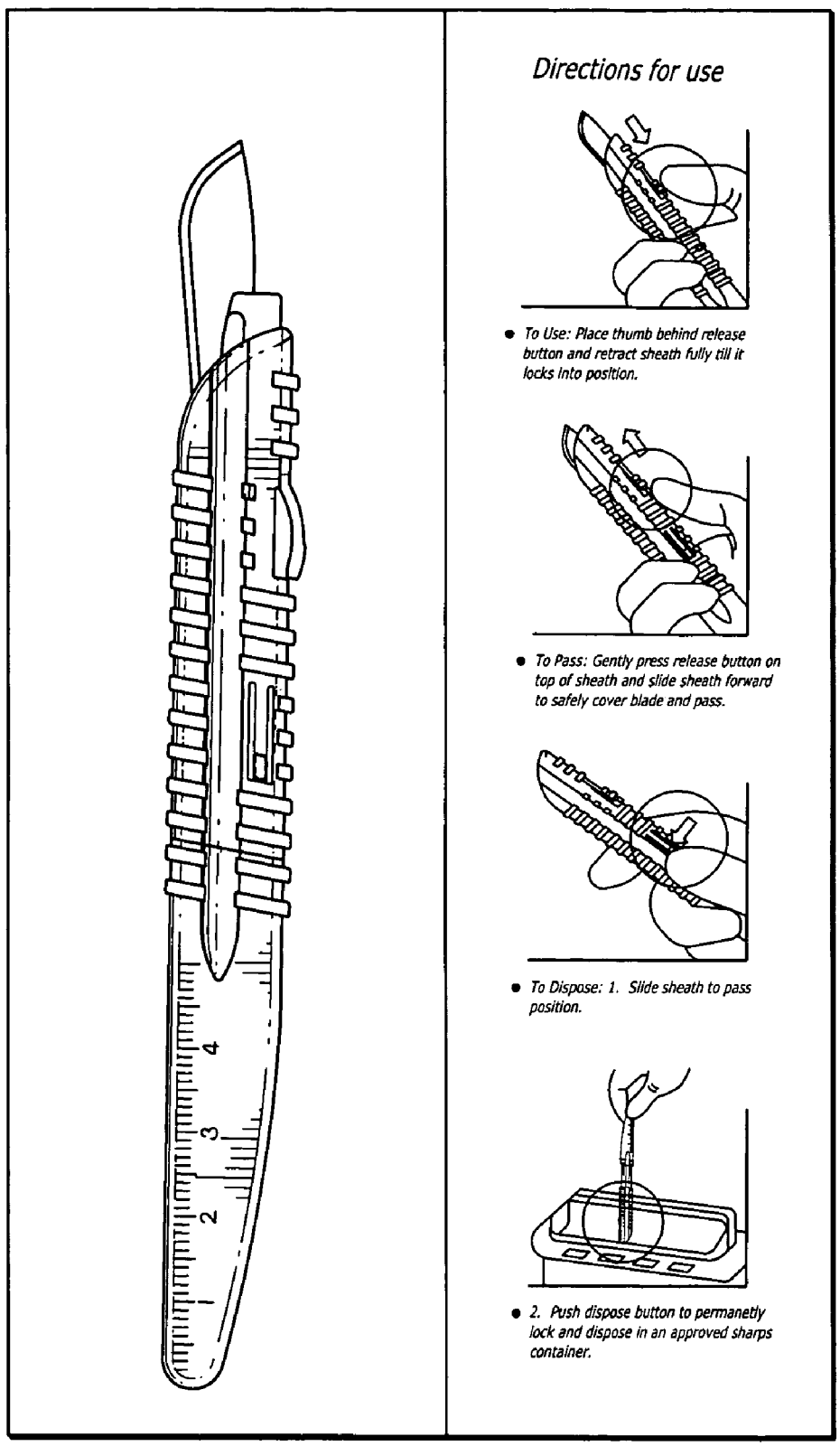
FIG. 13 is an exemplary embodiment of a brochure for the present invention showing directions for use.

FIG. 12 is another embodiment of the release button 514 of the scalpel. The elevated aspect of the release button 514 allows the sheath to be moved more easily. FIG. 13 is an exemplary embodiment of a brochure for the present invention showing directions for use of the scalpel.

Figure 14:
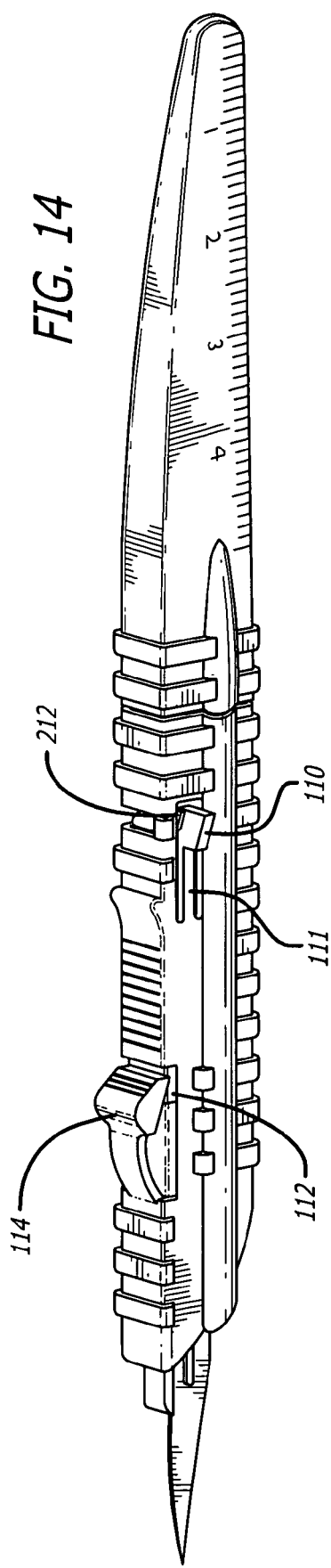
FIG. 14 is a view of the scalpel with alternate designs for the release button and the locking button, where the locking button has a tapered design.
Figure 15:
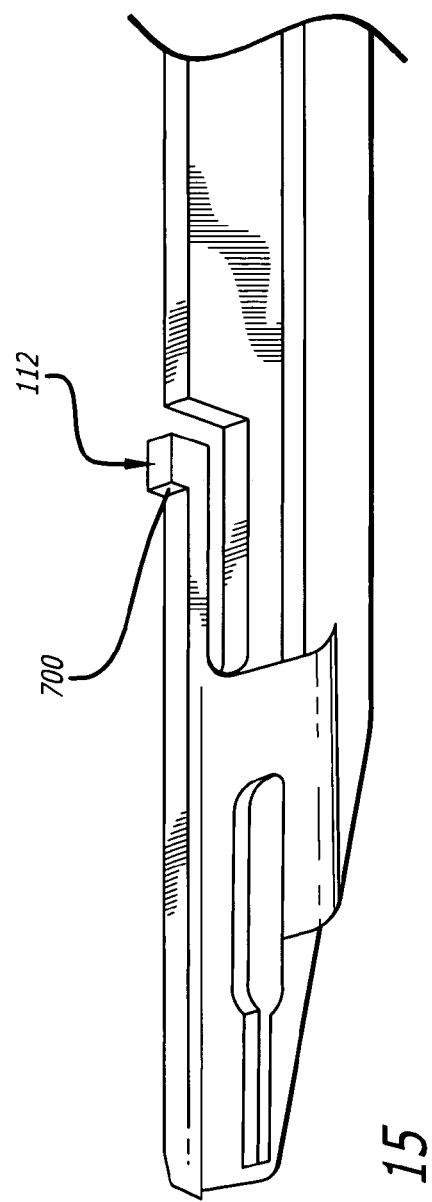
FIG. 15 is a view of the handle with an alternate design for one of the walls of the flexible locking strip.
Figure 16:
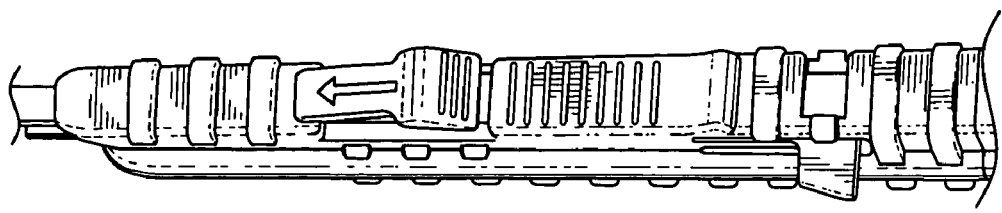
FIG. 16 is another view of the scalpel showing the tapered locking button.

FIGS. 14 and 16 are different views of the scalpel with differing designs for the release and the locking (or lockout) buttons, 114 and 110 respectively. Specifically, shown therein is a release button 114 residing on the flexible locking strip 112 when the sheath is in a retracted mode. As shown in FIG. 15, in this embodiment, the wall 700 of the flexible locking strip 112 is substantially more vertical as compared to the wall of the flexible strip 112 of FIG. 1g. To move the sheath forward, the release button 114 is depressed so as to deflect the flexible strip 112 downwards, thereby allowing the sheath to smoothly move to an extended mode where it covers the blade.

Furthermore, as shown in FIGS. 14 and 16, the design of the lockout button 110 and the wedge 212 is tapered and no longer parallel to the rails of the sheath (which correspond to the rails 103 of the handle) when the sheath is not locked to the handle. When button 110 is depressed into the opening 116, so as to lock the sheath to the handle, it becomes substantially parallel to the rails of the sheath (as will be further explained below in reference to FIGS. 17a–b). Thus, the wedge 212 engages along the entire length with the flexible locking strip thereby preventing the lockout button 110 on the sheath from springing back out once engaged with the flexible locking strip. This mechanism then prevents the flexible locking strip from flexing downwards and permitting the sheath from moving, thus disabling the scalpel and preventing it from being used again.

Figure 17A:
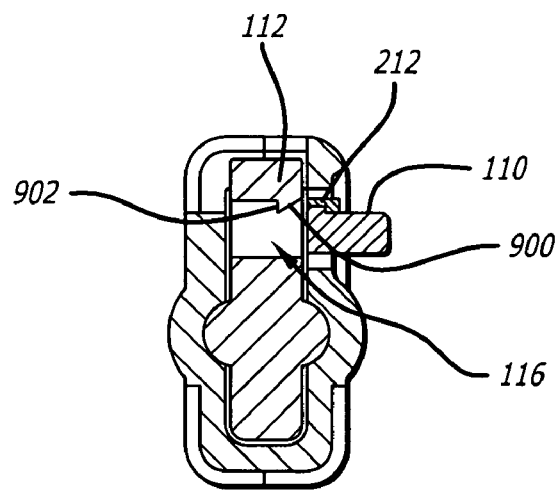
FIG. 17a is a close up view of the tapered design for the lockout button.
Figure 17B:
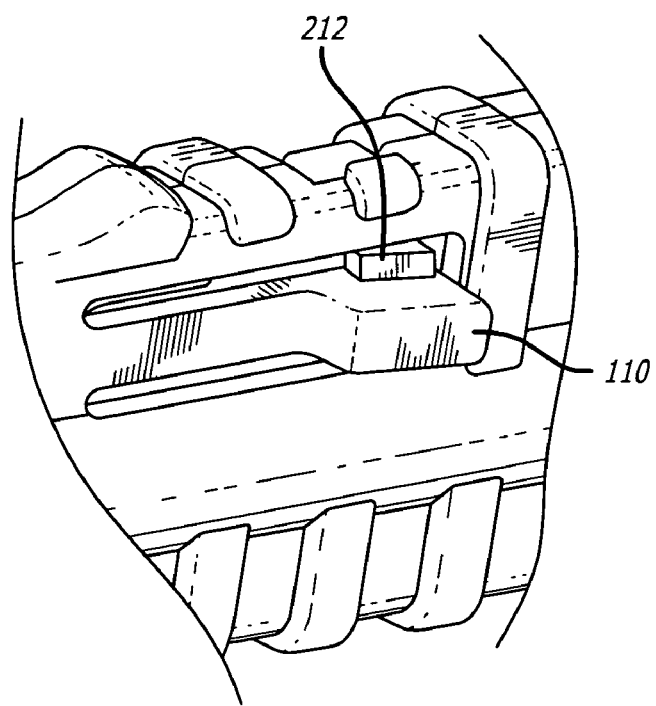
FIG. 17b is a cross-sectional view of the flexible locking strip in relation to the locking button when the sheath is to be permanently locked to the handle.

FIGS. 17a–b is a cross-sectional view and a close up view, respectively, of the tapered design for the lockout button. As can be seen in this design, the flexible locking strip has a ramp-like feature 900 with a wall 902. The button 110 with wedge 212, when depressed into the opening 116, slides along the ramp 900 and flexes upwards so that the wedge portion 212 engages the wall 902 of the flexible strip 112. In this state, the wedge portion is substantially parallel to the sheath rails (not shown). Thus, the wedge 212 engages the flexible locking strip thereby preventing the lockout button 110 on the sheath from springing back out once engaged with the flexible locking strip. This mechanism then prevents the flexible locking strip from flexing downwards and permitting the sheath from moving, thus disabling the scalpel and preventing it from being used again.

Furthermore, comparing the designs of FIGS. 1d and 17a, it can be seen that the lockout feature (or wedge) 212 does not have a ramp portion 210 in this embodiment of FIGS. 17a–b. Additionally, the flexible locking strip 112 in FIG. 17a has a ramp 900. This is in contrast to the design of FIG. 1d, where the flexible locking strip 112 does not include this ramp.

There are many advantages to the scalpel of the present invention. The present invention offers latched opened and closed positions in addition to a permanently locked position, requiring an additional locking mechanism. Additionally, there are several design aspects which make the scalpel of the present invention an improvement over the prior art. For example, the sheath of the present invention is designed such that it's shape is approximately an enclosed rectangle, thereby allowing the sheath to be as strong as possible so as to avoid breakage.

As described above, the handle of the scalpel has a rail which runs along either side, and the sheath similarly has a groove which runs along the inside and fits along the rail of the handle to facilitate its sliding movement and ensure proper fit. The rails not only facilitate the movement of the sheath but also provide structural strength and rigidity to the handle.

The attached description of exemplary and anticipated embodiments of the invention have been presented for the purposes of illustration and description. They are not intended to be exhaustive or to limit the invention to the precise forms disclosed. Many modifications and variations are possible in light of the teachings herein.

What is claimed:

1. A disposable scalpel comprising:
    a handle;
    a surgical blade attached to one end of the handle;
    a sheath covering at least a portion of the handle, movable between two positions:
        an open position wherein the blade is at least partly uncovered; and
        a closed position wherein the blade is substantially covered;
    a flexible locking strip attached to the handle for engaging the sheath in the open and closed positions;
    a first button attached to the sheath for releasing the flexible locking strip and allowing the sheath to be moved between the open and the closed position; and
    a second button attached to the sheath for permanently locking the sheath in the closed position.

2. The scalpel of claim 1 wherein the flexible locking snip sits in a first opening when the sheath is in the open position, said first opening being in the sheath.

3. The scalpel of claim 2 wherein the flexible locking strip sits in a second opening when the sheath is in the closed position, said second opening being in the sheath.

4. The scalpel of claim 3, wherein the second button sits in the second opening when the sheath is in the closed position.

5. The scalpel of claim 4, wherein the second button engages a portion of the flexible locking strip on one side when the sheath is in the closed position.

6. A disposable scalpel having a sheath, the sheath having three modes of operation:
    a protective mode where the sheath covers the blade, said sheath being made substantially immobile by means of a substantially flexible strip wherein the substantially flexible strip sits in a first opening when the sheath is in the open mode, said first opening being in the sheath; and
    an open mode where a blade connected to a handle of the scalpel can be used when the sheath is in a retracted position, and
    a permanently locked mode where the sheath covers the blade in permanently locked position, said locked position being achieved by depressing a locking button.

7. The scalpel of claim 6, wherein the substantially flexible strip sits in a second opening when the sheath is in the protective mode, said second opening being in the sheath.

8. The scalpel of claim 7, wherein the locking button sits in the second opening when the sheath is in the permanently locked mode.

9. The scalpel of claim 8, wherein the locking button engages a portion of the substantially flexible strip when the sheath is in the permanently locked mode.

10. The scalpel of claim 7 further including a release button for releasing the substantially flexible strip from the second opening so as to displace the sheath from the protective mode.

11. The scalpel of claim 6 wherein the handle comprises at least one rail along a first portion of the handle and the sheath comprises at least one groove along the inside of the sheath, the rail of the handle fitting into the groove of the sheath and facilitating the movement of the sheath.

12. The scalpel of claim 6 wherein the outside of the sheath has raised angular ridges.

13. The scalpel of claim 6 wherein the substantially flexible strip is a cantilever.

14. The scalpel of claim 6 further including a release button for releasing the substantially flexible snip from the first opening so as to displace the sheath from the open mode.

15. A disposable scalpel comprising:
a handle;
a surgical blade attached to one end of the handle;
a sheath covering at least a portion of the handle, movable between two positions:
   an open position wherein the blade is at least partly uncovered; and
   a closed position wherein the blade is substantially covered; and
a first button attached to the sheath for permanently locking the sheath in the closed position; and
a flexible locking strip attached to the handle for engaging the sheath in the open and closed positions.

16. The scalpel of claim 15 further including a second button attached to the sheath for releasing the flexible locking strip and allowing the sheath to be moved between the open and the closed position.

17. The scalpel of claim 15 wherein the flexible locking strip sits in a first opening when the sheath is in the open position, said first opening being in the sheath.

18. The scalpel of claim 15 wherein the flexible locking scrip sits in a second opening when the sheath is in the closed position, said second opening being in the sheath.

19. The scalpel of claim 18, wherein the first button sits in the second opening when the sheath is in the closed position.

20. The scalpel of claim 19, wherein the first button engages a portion of the flexible locking strip when the sheath is in the closed position.

* * * * *